(12) United States Patent
Fisher

(10) Patent No.: US 7,291,605 B2
(45) Date of Patent: *Nov. 6, 2007

(54) METHODS OF TREATING VARIOUS CANCERS USING MELANOMA DIFFERENTIATION ASSOCIATED PROTEIN-7

(75) Inventor: Paul B Fisher, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/048,543

(22) Filed: Jan. 31, 2005

(65) Prior Publication Data

US 2005/0191277 A1    Sep. 1, 2005

Related U.S. Application Data

(63) Continuation of application No. 09/991,452, filed on Nov. 21, 2001, now Pat. No. 6,855,686, which is a continuation of application No. 09/251,124, filed on Feb. 16, 1999, now Pat. No. 6,355,622, which is a continuation of application No. PCT/US97/14548, filed on Aug. 15, 1997, which is a continuation-in-part of application No. 08/696,573, filed on Aug. 16, 1996, now Pat. No. 5,710,137.

(51) Int. Cl.
| | |
|---|---|
| A01N 43/04 | (2006.01) |
| A01N 63/00 | (2006.01) |
| C12N 15/00 | (2006.01) |
| C12N 15/63 | (2006.01) |
| C07H 21/04 | (2006.01) |

(52) U.S. Cl. .................. 514/44; 424/93.21; 435/320.1; 435/455; 536/23.5; 536/24.1

(58) Field of Classification Search .................. 514/44; 435/320.1, 455; 424/93.2, 93.21; 536/23.5, 536/24.1
See application file for complete search history.

(56) References Cited

U.S. PATENT DOCUMENTS

| 5,480,968 | A | | 1/1996 | Kraus et al. | |
|---|---|---|---|---|---|
| 5,643,761 | A | | 7/1997 | Fisher et al. | |
| 5,710,137 | A | * | 1/1998 | Fisher | 514/44 |
| 6,190,909 | B1 | | 2/2001 | Levinson et al. | |
| 6,355,622 | B1 | * | 3/2002 | Fisher | 514/44 |
| 6,720,408 | B2 | | 4/2004 | Fisher et al. | |

FOREIGN PATENT DOCUMENTS

| WO | WO95/11986 | 5/1995 |
|---|---|---|
| WO | WO98/06441 | 2/1998 |
| WO | WO00/55310 | 9/2000 |
| WO | WO01/05437 | 1/2001 |

OTHER PUBLICATIONS

Rudinger, 1976, Peptide Hormones, Edited by Parsons, University Park Press, Baltimore, p. 1-7.*
Kaye et al., 1990, Proc. Natl. Acad. Sci. USA, vol. 87, pp. 6922-6926.*
Skolnick et al., 2000, Trends in Biotech, vol. 18, p. 34-39.*
Deonarain, 1998, Expert Opin. Ther. Pat., vol. 8, pp. 53-69.*
Verma, Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Cunningham et al. Mol. Ther. (2005), 149-159. Clinical and Logical Effects of an Intratumoral Injection of mda-7 (IL24; INGN 241) in Patients with Advanced Carcinoma: A Phase I Study.
Lebedeva et al. Mol. Ther. (2005), 4-18. mda-7/IL 24: Exploiting Cancer's Achilles' Heel.
Tong et al. Molecular Therapy (2005), 160-172. Intratumoral Injection of INGN 241, A Nonreplicating Adenovector Expressing the Melanoma-Dofferentation Associated Gene-7 (mda-7/IL24): Niologic Outcome in Advanced Cancer Patients.
Introgen Therapeutics, Inc. Press release Jun. 7, 2004. Introgen Presents Final Data From INGN 241 Phase I Study, Demonstrating Clinical and Biologic Activity.
Chen, J. et al. Mol Ther. (2003), 8:220-229. Tumor suppressor MDA-7/IL-24 selectively inhibits vascular smooth muscle cell growth and migration.
Fisher et al., Cancer Biol. and Ther. (2003), 2:Suppl. 1, S23-37. 2003. Mda-7/IL-24, a novel cancer selective apoptosis inducing cytokine gene: From the laboratory to the clinic.
Introgen Therapeutics, Inc., Press release, Sep. 25, 2003. Publication shows Introgen's INGN 241 drug overcomes common cancer toxicity pathways.
Prochazkova et al., (2003). Comparative study of apoptosis-detecting techniques: TUNEL, apostain, and lamin B. Biotechniques 35(3):528-534.

(Continued)

*Primary Examiner*—Shin-Lin Chen
(74) *Attorney, Agent, or Firm*—Baker Botts L.L.P.

(57) ABSTRACT

This invention provides a method for reversing the cancerous phenotype of a cancer cell by introducing a nucleic acid having the melanoma differentiation associated gene (mda-7) into the cell under conditions that permit the expression of the gene so as to thereby reverse the cancerous phenotype of the cell. This invention also provides a method for reversing the cancerous phenotype of a cancer cell by introducing the gene product of the above-described gene into the cancerous cell so as to thereby reverse the cancerous phenotype of the cell. This invention also provides a pharmaceutical composition having the melanoma differentiation associated gene (mda-7) or the gene product of the melanoma differentiation associated gene (mda-7) effective to reverse the cancerous phenotype of a cancer cell and a pharmaceutically acceptable carrier.

1 Claim, 6 Drawing Sheets

OTHER PUBLICATIONS

Sauane, M. et al.. J Cell Physiol. (2003), 196:334-345. Mda-7/IL-24 induces apoptosis of diverse cancer cell lines through JAK/STAT-independent pathways.

Waxman et al., (2003). Harnessing apoptosis for improved anticancer gene therapy. Cancer Research 63:8563-8572.

Cao, X. X. et al.. Mol Med. (2002), 8:869-876. Adenoviral transfer of mda-7 leads to BAX up-regulation and apoptosis in mesothelioma cells, and is abrogated by over-expression of BCL-XL.

Kawabeet al. (2002). Adenovirus-mediated mda-7 gene expression radiosensitizes non-small cell lung cancer cells via TP53-independent mechanisms. Mol Ther. 6(5):637-644.

Saeki et al., (2002). Inhibition of human lung cancer growth following adenovirus-mediated mda-7 gene expression in vivo. Oncogene 21(29):4558-4566.

Smyth et al., (2002). Markers of apoptosis: methods for elucidating the mechanism of apoptotic cell death from the nervous system. Biotechniques 32(3):648-665.

Mhashilkar A. M. et al. Mol Med. (2001), 7:271-282. Melanoma differentiation associated gene-7 (mda-7): a novel anti-tumor gene for cancer gene therapy.

Saeki et al., (2000). Tumor-suppressive effects by adenovirus-mediated mda-7 gene transfer in non-small cell lung cancer cell in vitro. Gene Ther. 7(23):2051-2057.

Green (1998). Apoptotic pathways: the roads to ruin. Cell 94:695-698.

Kang, D. et al. (1998). Reciprocal Subtraction Differential RNA Display: An Efficient And Rapid Procedure For Isolating Differentially Expressed Gene Sequences. Proc Natl Acad Sci U S A 95, 13788-13793.

Su, Z. Z. et al. (1998). The Cancer Growth Suppressor Gene Mda-7 Selectively Induces Apoptosis In Human Breast Cancer Cells And Inhibits Tumor Growth In Nude Mice. Proc Natl Acad Sci U S A 95, 14400-14405.

Jiang, H. et al. (1996). The Melanoma Differentiation Associated Gene Mda-7 Suppresses Cancer Cell Growth. Proc Natl Acad Sci U S A 93, 9160-9165.

Jiang, H. et al. (1995). Cell Cycle Gene Expression And E2F Transcription Factor Complexes In Human Melanoma Cells Induced To Terminally Differentiate. Oncogene 11, 1179-1189.

Jiang, H. et al. (1995) Subtraction Hybridization Identifies A Novel Melanoma Differentiation Associated Gene, mda-7, Modulated During Human Melanoma Differentiation, Growth and Progression. Oncogene;11(12):2477-2486.

Jiang H. et al. (1995) The Melanoma Differentiation-Associated Gene Mda-6, Which Encodes The Cyclin-Dependent Kinase Inhibitor p21, Is Differentially Expressed During Growth, Differentiation, And Progression In Human Melanoma Cells. Oncogene;10(9):1855-1864.

Fisher, P. B. Human MDA-7 (mda-7) mRNA, Complete Cds. GenBank Accession No. U16261. Deposited (1994).

Jiang, H., et al. (1994). A Molecular Definition Of Terminal Cell Differentiation In Human Melanoma Cells. Mol Cell Different 2, 221-239.

Su, Z. Z., et al. (1994). Induction Of Transformation Progression In Type 5 Adenovirus-Transformed Rat Embryo Cells By A Cloned Protein Kinase C Beta 1 Gene And Reversal Of Progression By 5-Azacytidine. Oncogene 9, 1123-1132.

Hara E, et al. (1993) DNA-DNA Subtractive cDNA Cloning Using Oligo(dT)30-Latex And PCR: Identification Of Cellular Genes Which Are Overexpressed In Senescent Human Diploid Fibroblasts. Anal Biochem; 214(1):58-64.

Jiang, H., et al. (1993). Regulation Of c-foc, c-jun And jun-B Gene Expression In Human Melanoma Cells Induced To Terminally Differentiate. Mol Cell Different 1, 197-214.

Jiang H, et al. (1993) Use Of A Sensitive And Efficient Subtraction Hybridization Protocol For The Identification Of Genes Differentially Regulated During The Induction Of Differentiation In Human Melanoma Cells. Mol Cell Different;1:285-299.

Reddy, PG, et al. (1993). Identification And Cloning Of Genes Involved In Progression Of Transformed Phenotype. In: Chromosome and Genetic Analysis, Methods in Molecular Genetics, vol. 1, K. W. Adolph, ed. (Orlando, FL, Academic Press Inc.), pp. 68-102.

Su, Z. Z., et al. (1993). Defining The Critical Gene Expression Changes Associated With Expression And Suppression Of The Tumorigenic And Metastatic Phenotype In Ha-ras-Transformed Cloned Rat Embryo Fibroblast Cells. Oncogene 8, 1211-1219.

Su, ZZ, et al. (1993). Genetic Analysis Of Carcinogen Enhancement Of Type 5 Adenovirus Transformation Of Cloned Fischer Rat Embryo Fibroblast Cells. Mol Carcinog 8, 155-166.

Su, ZZ, et al. (1993). Wild-Type Adenovirus Type 5 Transforming Genes Function As Transdominant Suppressors Of Oncogenesis In Mutant Adenovirus Type 5 Transformed Rat Embryo Fibroblast Cells. Cancer Res 53, 1929-1938.

Su, Z. Z. et al. (1992). Transfer Of A Dominant-Acting Tumor-Inducing Oncogene From Human Prostatic Carcinoma Cells To Cloned Rat Embryo Fibroblast Cells By DNA-Transfection. Anticancer Res;12(2):297-304.

Hara, E. et al. (1991). Subtractive cDNA Cloning Using oligo(dT)30-latex And PCR: Isolation Of cDNA Clones Specific To Undifferentiated Human Embryonal Carcinoma Cells. Nucleic Acids Res;19(25):7097-7104.

Herfort MR, et al. (1991). Simple And Efficient Subtractive Hybridization Screening. Biotechniques;11(5):598, 600, 602-604.

Lee S.W., et al. (1991). Positive Selection Of Candidate Tumor-Suppressor Genes By Subtractive Hybridization. Proc Natl Acad Sci USA;88(7):2825-2829.

Su, Z. Z., et al. (1991). Suppression Of Adenovirus Type 5 E1A-Mediated Transformation And Expression Of The Transformed Phenotype By Caffeic Acid Phenethyl Ester (CAPE). Mol Carcinog 4, 231-242.

Su, Z. Z., et al. (1990). Enhancement Of Adenovirus Transformation Of Cloned Rat Embryo Fibroblast Cells By Gamma Irradiation. Mol Carcinog 3, 141-149.

Wieland I, et al. (1990). A Method For Difference Cloning: Gene Amplification Following Subtractive Hybridization Proc Natl Acad Sci USA;87(7):2720-2724.

Duguid, J. R. et al. (1988). Isolation Of cDNAs Of Scrapie-Modulated RNAs By Subtractive Hybridization Of A cDNA Library. Proc Natl Acad Sci USA;85(15):5738-5742.

Sive, H. L. et al. (1988). A Simple Subtractive Hybridization Technique Employing Photoactivatable Biotin And Phenol Extraction. Nucleic Acids Res;16(22):10937.

Travis, G. H. et al.. (1988). Phenol Emulsion-Enhanced DNA-Driven Subtractive Cdna Cloning: Isolation Of Low-Abundance Monkey Cortex-Specific mRNAs. Proc Natl Acad Sci USA;85(5):1696-1700.

Maniatis, T. et al. (1982) "Strategies For cDNA Cloning" *Molecular Cloning: A Laboratory Manual*, Cold Spring Harbor Laboratory, 224-228.

* cited by examiner

METHODS OF TREATING VARIOUS CANCERS USING MELANOMA DIFFERENTIATION ASSOCIATED PROTEIN-7

CROSS REFERENCE TO RELATED APPLICATIONS

This application claims priority to the following applications: the instant application is a continuation application of U.S. patent application Ser. No. 09/991,452 filed Nov. 21, 2001, now U.S. Pat. No. 6,855,686, which is a continuation of U.S. patent application Ser. No. 09/251,124 filed Feb. 16, 1999, now U.S. Pat. No. 6,355,622, which is a continuation application of International Patent Application PCT/US97/14548, filed Aug. 15, 1997, which is a continuation-in-part of U.S. patent application Ser. No. 08/696,573, filed Aug. 16, 1996, now U.S. Pat. No. 5,710,137, each of which are incorporated by reference in their entireties herein.

STATEMENT REGARDING FEDERALLY SPONSORED RESEARCH

The invention disclosed herein was made with Government support under NC/NIGH Grant No. CA35675 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of each series of experiments.

BACKGROUND OF THE INVENTION

Cancer is a complex multi factor and multi step process involving the coordinated expression and suppression of genes functioning as positive and negative regulators of oncogenes is (1-5). Direct cloning strategies, based on transfer of a dominant transforming or tumorigenic phenotype, have identified positive acting oncogenes (6-9). In contrast, the detection and cloning of genes that suppress the cancer phenotype have proven more difficult and elusive (10-15). A direct approach for isolating genes directly involved in regulating growth and differentiation involves subtraction hybridization between cDNA libraries constructed from actively growing cancer cells and cDNA libraries from cancer cells induced to lose proliferative capacity irreversibly and terminally differentiate (13,14). This experimental strategy has been applied to human melanoma cells, induced to terminally differentiate by treatment with recombinant human interferon β (IFN-β) and mezerein (MEZ), resulting in the cloning of novel melanoma differentiation-associated (mda) genes not previously described in DNA data bases (13,14). A direct role for specific mda genes in mediating growth and cell cycle control is apparent by the identification and cloning of mda-6 (13-16), which is identical to the ubiquitous inhibitor of cyclin-dependent kinases p21 (17). The importance of p21 in growth control is well documented and this gene has been independently isolated, as WAF-1, CIP-1, and SDI-1, by a number of laboratories using different approaches (18-20). These studies indicate that specific genes associated with proliferative control are induced and may contribute to the processes of growth arrest and terminal differentiation in human cancer cells.

The mda-7 gene was cloned from a differentiation inducer (IFN-β plus MEZ)-treated human melanoma (H0-1) subtracted library (13,14). The full-length mda-7 cDNA is 1718 nucleotides, and the major open reading frame encodes a novel protein of 206 aa with an $M_r$ of 23.8 kDa (21). Previous studies indicate that mda-7 is induced as a function of growth arrest and induction of terminal differentiation in human melanoma cells (14,21). mda-7 expression also inversely correlates with melanoma progression—i.e., actively growing normal human melanocytes express more mda-7 than metastatic human melanoma cells (21). Moreover, mda-7 is growth inhibitory toward human melanoma cells in transient transfection assays and in stable transformed cells containing a dexamethasone (DEX)-inducible mda-7 gene (21). These studies indicate that mda-7 may contribute to the physiology of human melanocytes and melanomas, and this gene has growth suppressive properties when overexpressed in human melanoma cells.

The mda-7 gene was also described in the International Patent Cooperation Treaty Application No. PCT/US94/12160, international filing date, Oct. 24, 1994 with Internation Publication No. WO95/11986, the content of which is incorporated into this application by reference.

This invention reports that mda-7 is a potent growth suppressing gene in cancer cells of diverse origin, including breast, central nervous system, cervix, colon, prostate and connective tissue. An inhibition in colony formation occurs in cancer cells containing defects in their p53 and/or retinoblastoma (RB) genes or lacking p53 and RB expression. In contrast, expression of mda-7 in normal human mammary epithelial cells, human skin fibroblasts and rat embryo fibroblasts induces quantitatively less growth suppression than in cancer cells. When stably expressed in human cervical carcinoma (HeLa) and prostate carcinoma (DU-145) cells, mda-7 has a negative effect on growth and transformation-related properties. The effects of mda-7 on HeLa cells are reversible following abrogation of the MDA-7 protein by infection with a genetically modified Ad5 vector expressing an antisense mda-7 gene. These observations indicate that mda-7 is a novel growth suppressing gene with a wide range of inhibitory actions in human cancers manifesting different genetic defects.

SUMMARRY OF THE INVENTION

This invention provides a method for reversing the cancerous phenotype of a cancer cell by introducing a nucleic acid including a melanoma differentiation associated gene (mda-7) into the cell under conditions permitting the expression of the gene so as to thereby reverse the cancerous phenotype of the cell. This invention also provides a method for reversing the cancerous phenotype of cancer cell in a subject by introducing the above-described nucleic acid into the subject's cancerous cell.

This invention also provides a method for reversing the cancerous phenotype of a cancer cell by introducing the gene product of a melanoma differentiation associated gene (mda-7) into the cancer cell so as to thereby reverse the cancerous phenotype of the cell. This invention also provides a method for reversing the cancerous phenotype of a cancer cell in a subject by introducing the above-described gene product into the subject's cancerous cell.

This invention also provides a pharmaceutical composition having an amount of a nucleic acid including a melanoma differentiation associated gene (mda-7) effective to reverse the cancerous phenotype of a cancer cell and a pharmaceutically acceptable carrier. This invention also provides a pharmaceutical composition having an amount of the gene product of the above-described gene effective to reverse the cancerous phenotype of a cancer cell and a pharmaceutically acceptable carrier.

BRIEF DESCRIPTION OF THE FIGURES

FIG. 4A. Cells were grown in the absence or presence of $10^{-6}$ M DEX for 96 hr, and total RNA was isolated, subjected to Northern blotting and probed with mda-7, a neomycin resistance (Neo$^R$) gene and GAPDH.

FIG. 4B. Cells were grown in the absence or presence of $10^{-6}$ M DEX for 96 hr, cellular proteins were labeled with [$^{35}$S] methionine and immunoprecipitated with antibodies recognizing MDA-7 and actin proteins.

DETAILED DESCRIPTION OF THE INVENTION

Figure 1:
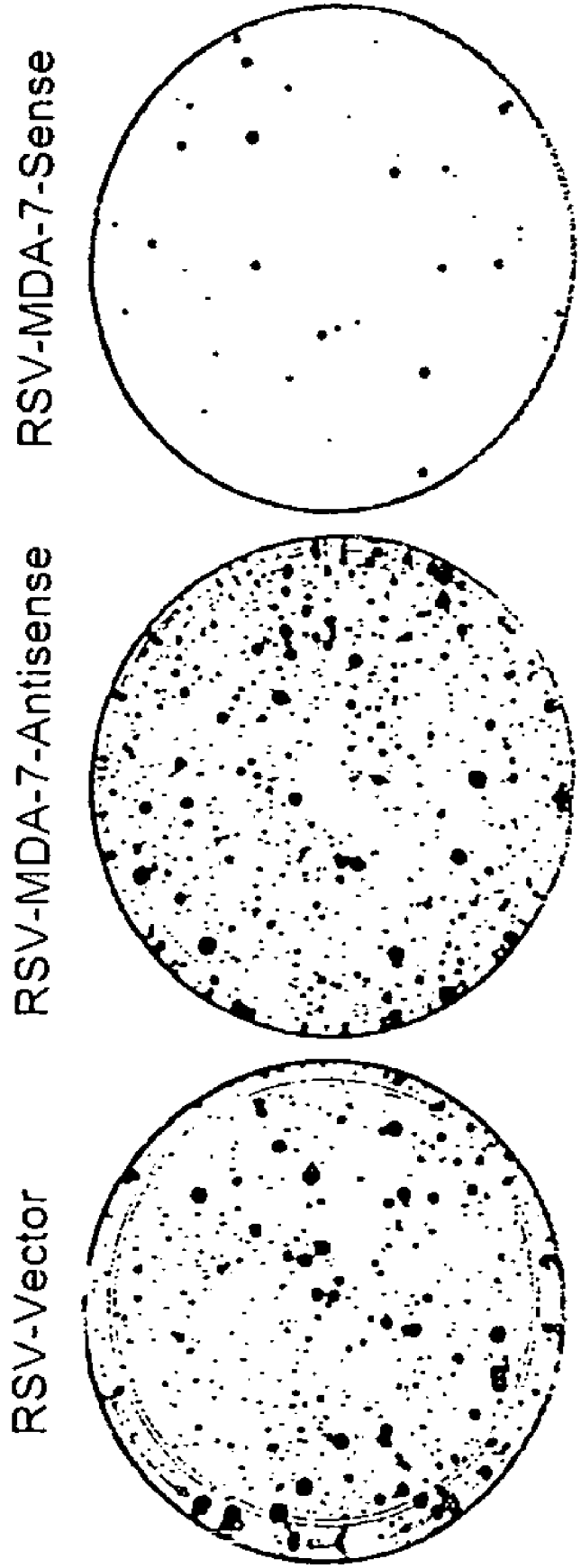
FIG. 1. Effect of mda-7 expression on hygromycin resistant colony formation in HeLa cells. HeLa cells were transfected with 10 µg of pREP4 vector (RSV-vector), mda-7 cloned in an antisense orientation in the pREP4 vector (RSV-MDA-7-Antisense), or mda-7 cloned in a sense orientation in the pREP4 vector (RSV-MDA-7-Sense) and selected in media containing 100 µg of hygromycin.

In order to facilitate an understanding of the Experimental Details section which follows, certain frequently occurring methods and/or terms are described in Sambrook, et al. (45).

This invention provides a method for reversing the cancerous phenotype of a cancer cell which comprises introducing a nucleic acid comprising a melanoma differentiation associated gene (mda-7) into the cell under conditions permitting the expression of the gene so as to thereby reverse the cancerous phenotype of the cell.

This invention also provides a method for reversing the cancerous phenotype of a cancer cell in a subject which comprises introducing a nucleic acid molecule comprising a melanoma differentiation associated gene (mda-7) into the subject's cancerous cell under conditions permitting expression of the gene in the subject's cells so as to thereby reverse the cancerous phenotype of the cell.

Methods to introduce a nucleic acid molecule into cells have been well known in the art. Naked nucleic acid molecule may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, mechanical or electrical means. The above recited methods are merely served as examples for feasible means of introduction of the nucleic acid into cells. Other methods known may be also be used in this invention.

In an embodiment of the above methods, the melanoma differentiation associated gene (mda-7) is linked to a regulatory element such that its expression is under the control of the regulatory element. In a still further embodiment, the regulatory element is inducible or constitutive. Inducible regulatory element like an inducible promoter is known in the art. Regulatory element such as promoter which can direct constitutive expression is also known in the art.

In a separate embodiment, the regulatory element is a tissue specific regulatory element. The expression of the mda-7 gene will then be tissue-specific.

In another embodiment of the above-described methods, the cancer cell is characterized by the presence within the cancer cell of a defective tumor suppressor gene. The defective tumor suppressor gene includes, but is not limited to, a p53, a retinoblastoma (RB) or a p16$^{ink4a}$ gene.

In an embodiment of the above-described methods, the cancer cell is characterized by the presence within the cancer cell of a dominant acting oncogene. Specifically, the dominant acting oncogene may be a Ha-ras, mutant p53 or human papilloma virus genes. The Ha-ras is a Harvey virus ras oncogene.

In an embodiment of the above methods, the nucleic acid comprises a vector. The vector includes, but is not limited to, an adenovirus vector, adeno-associated virus vector, Epstein-Barr virus vector, Herpes virus vector, attenuated HIV vector, retrovirus vector and vaccinia virus vector. In a preferred embodiment, the adenovirus vector is a replication-defective adenovirus vector expressing mda-7, designated Ad.mda-7 S. In another embodiment, the adenovirus vector is a replication-competent adenovirus vector.

This invention also provides a method for reversing the cancerous phenotype of a cancer cell which comprises introducing the gene product of a melanoma differentiation associated gene (mda-7) into the cancerous cell so as to thereby reverse the cancerous phenotype of the cell.

This invention further provides a method for reversing the cancerous phenotype of a cancer cell in a subject which comprises introducing the gene product of a melanoma differentiation associated gene (mda-7) into the subject's cancerous cell so as to thereby reverse the cancerous phenotype of the cell.

In an embodiment of the above-described methods, the cancer cell includes, but is not limited to, a breast, cervical, colon, prostate, nasopharyngeal, lung connective tissue or nervous system cell. The cancer cell further includes cells from glioblastoma multiforme, lymphomas and leukemia.

This invention also provides a pharmaceutical composition which comprises an amount of a nucleic acid comprising a melanoma differentiation associated gene (mda-7) effective to reverse the cancerous phenotype of a cancer cell and a pharmaceutically acceptable carrier.

As used herein, the term "pharmaceutically acceptable carrier" encompasses any of the standard pharmaceutical carriers. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In an embodiment, the nucleic acid comprises a vector. The vector includes, but is not limited to, an adenovirus vector, adeno-associated virus vector, Epstein-Barr virus vector, Herpes virus vector, attenuated HIV virus, retrovirus vector and vaccinia virus vector. In a preferred embodiment, the adenovirus vector is a replication-defective adenovirus vector expressing mda-7, designated Ad.mda-7 S. In another embodiment, the adenovirus is a replication-competent adenovirus vector.

This invention also provides a pharmaceutical composition comprising an amount of the gene product of a melanoma differentiation associated gene (mda-7) effective to reverse the cancerous phenotype of a cancer cell and a pharmaceutically acceptable carrier.

In an embodiment of the above-described methods, the cancer cell includes, but is not limited to, a breast, cervical, colon, prostate, nasopharyngeal, lung connective tissue and nervous system cells. The cancer cell further includes cells from glioblastoma multiforme, lymphomas and leukemia.

This invention will be better understood from the Experimental Details which follow. However, one skilled in the art will readily appreciate that the specific methods and results discussed are merely illustrative of the invention as described more fully in the claims which follow thereafter.

Experimental Details

Cancer is a disease characterized by defects in growth control, and tumor cells often display abnormal patterns of cellular differentiation. The combination of recombinant human fibroblast interferon and the antileukemic agent mezerein corrects these abnormalities in cultured human melanoma cells resulting in irreversible growth arrest and terminal differentiation. Subtraction hybridization identifies a melanoma differentiation associated gene (mda-7) with elevated expression in growth arrested and terminally differentiated human melanoma cells. Colony formation decreases when mda-7 is transfected into human tumor cells of diverse origin and with multiple genetic defects. In contrast, the effects of mda-7 on growth and colony formation in transient transfection assays with normal cells, including human mammary epithelial, human skin fibroblast and rat embryo fibroblast, is quantitatively less than that found with cancer cells. Tumor cells expressing elevated mda-7 display suppression in monolayer growth and anchorage independence. Infection with a recombinant type 5 adenovirus expressing antisense mda-7 eliminates mda-7 suppression of the in vitro growth and transformed phenotype. The ability of mda-7 to suppress growth in cancer cells not expressing or containing defects in both the retinoblastoma (RB) and p53 genes indicates a lack of involvement of these critical tumor suppressor elements in mediating mda-7-induced growth inhibition. The lack of protein homology of mda-7 with previously described growth suppressing genes and the differential effect of this gene on normal versus cancer cells suggests that mda-7 may represent a new class of cancer growth suppressing genes with antitumor activity.

Materials and Methods

Cell Lines and Culture Conditions. Human carcinoma cell lines, including MCF-7 and T47D (breast), LS174T and SW480 (colorectal), HeLa (cervical), DU-145 (prostate), and HONE-1 (nasopharyngeal) (9,22-25), were grown in Dulbecco's modified Eagle's medium supplemented with 10% fetal bovine serum (DMEM-10) at 37° C. in a 5% $CO_2$/95% air-humidified incubator. Additional human cell types including HBL-100 (normal mammary epithelial), H0-1 and C8161 (melanoma), GBM-18 and T98G (glioblastoma multiforme) and Saos-2 (human osteosarcoma) were maintained under similar conditions. Early passage normal human mammary epithelial cells (HMEC; passages 10-12) were obtained from Clonetics Corporation (San Diego, Calif.). HMEC cells were maintained in serum-free medium as described by Clonetics Corporation. CREF-Trans 6 (cloned Fischer rat embryo fibroblast) (9,26) and CREF Ha-ras (CREF cells transformed by the Ha-ras (T24) oncogene) (27) were cultured in DMEM-5. HeLa cl 1 is a hygromycin resistant ($Hyg^R$) Rous Sacroma virus RSV vector (pREP4) (Invitrogen) transformed HeLa clone. HeLa cl 2 is a $Hyg^R$ mda-7 expressing HeLa clone. HeLa cl 1 and HeLa cl 2 cells were constructed as described (12,21) and maintained in DMEM-10 containing 100 µg/ml of hygromycin. DU-145 cl 6 and DU-145 cl 7 cells contain a DEX-inducible mda-7 gene (cloned in a pMAMneo vector) (Clontech) (21) and are maintained in DMEM-10 containing 200 µg/ml G418.

Subtraction Hybridization, Plasmids, Expression Vector Constructs, and Northern Hybridization. Identification and cloning of mda-7 by subtraction hybridization was achieved as described (13). A full-length mda-7 cDNA was isolated by screening a recombinant IFN-β plus MEZ-treated H0-1 cDNA library (13) and using the procedure of rapid amplification of cDNA ends as described (15). An mda-7 cDNA fragment (nucleotide position 176-960) containing the open reading frame was amplified with PCR and cloned into PCRII™ (Invitrogen) by TA cloning. The orientation of the inserts in the vectors was determined by restriction mapping. The human cell expression constructs were made by cloning Kpn I-Xho I fragments from the PCR™ vectors into pREP4 vector (Invitrogen) downstream of a RSV promoter in a sense [mda-7 (S)] or antisense [mda-7 (AS)] orientation. Alternatively, the mda-7 gene fragment was cloned into the pMAMneo (Clontech) vector in a sense and antisense orientation. RNA isolation and Northern blotting were performed as described (9,12,13,21).

Monolayer Growth, Anchorage-Independence and DNA-Transfection Assays. Monolayer and anchorage-independent growth assays were performed as previously described (8,12,26). To study the effect of mda-7 on monolayer colony formation the vector [pREP4 (RSV)] containing no insert, mda-7 (S) or mda-7 (AS) expression constructs were transfected into the various cell types by the lipofectin method (GIBCO/BRL) and hygromycin resistant colony formation or cell growth in hygromycin was determined (12,21).

Construction of Antisense-mda-7 Adenovirus Vector. The recombinant replication-defective Ad.mda-7 (AS) was created in two steps. First, the coding sequence of the mda-7 gene was cloned into a modified Ad expression vector pAd.CMV (28). This contains, in order, the first 355 bp from the left end of the Ad genome, the cytomegalovirus (CMV) immediate early promoter, DNA encoding splice donor and acceptor sites, cloning sites for the desired gene (in this case mda-7), DNA encoding a polyA signal sequence from the beta globin gene, and approximately 3 kbp of adenovirus sequence extending from within the E1B coding region. This arrangement allows high level expression of the cloned sequence by the CMV immediate early gene promoter, and appropriate RNA processing (28). The recombinant virus was created in vivo in 293 cells (29) by homologous recombination between mda-7-containing vector and plasmid JM17, which contains the whole of the Ad genome cloned into a modified version of pBR322 (30). JM17 gives rise to Ad genomes in vivo but they are too large to package. This constraint is relieved by recombination with the vector to create a packageable genome (30), containing the gene of choice. The recombinant virus is replication defective in human cells except, 293 cells, which express adenovirus E1A and E1B. Following transfection of the two plasmids, infectious virus was recovered, the genomes were analyzed to confirm the recombinant structure, and then virus was plaque purified, all by standard procedures (31).

Peptide Antibody Production and Immunoprecipitation Analyses. Peptide antibodies were prepared against PSQEN-EMFSIRD as described (21). Logarithmically growing HeLa, HeLa cl 1 (Hyg$^R$ pREP4 vector control HeLa clone), and HeLa cl 2 [pREP4-mda-7 (S) transfected Hyg$^R$ mda-7 expressing HeLa clone] cells were either untreated or infected with 10 plaque forming units of control adenovirus (H5dl434) (32) or a recombinant adenovirus expressing mda-7 (AS) [Ad.mda-7 (AS)]. At various times after infection, cultures were starved of methionine for 1 hr at 37° C. in methionine-free medium, cells were concentrated by pelleting and labeled for 4 hr at 37° C. in 1 ml of the same medium with 100 µCi (1 Ci=37 GBq) of $^{35}$S (NEN; Express $^{35}$S). Immunoprecipitation analyses with 2 µg of MDA-7 peptide rabbit polyclonal antibody or actin monoclonal antibody (Oncogene Sciences) were performed as described (15,21).

Experimental Results

Enhanced Growth Inhibitory Properties of mda-7 in Human Cancer Cells and Ha-ras-Transformed Rat Embryo Fibroblast Cells. DNA transfection assays were performed to evaluate the effect of elevated expression of mda-7 on cell growth. When transfected into human cervical carcinoma (HeLa) cells, the mda-7 (S) construct results in a 10-to 15-fold reduction in Hyg$^R$ colonies in comparison with the pREP4 vector and mda-7 (AS) construct transfected cultures (FIG. 1 and Table 1).

TABLE 1

Effect of mda-7 on monolayer colony formation of human cancer, normal rat embryo fibroblast (CREF) and Ha-ras-transformed CREF cells.

| Cell Type | RSV-Vector[a] | RSV-mda-7(S)[b] | RSV-mda-7(AS) |
|---|---|---|---|
| Human cancer cell lines[c] | | | |
| MCF-7 (Breast- Ca) | 118 ± 24 | 42 ± 16 (3.5) | 146 ± 20 |
| T47D (Breast- Ca) | 172 ± 9 | 44 ± 7 (4.2) | 186 ± 28 |
| HeLa (Cervix- Ca) | 1571 ± 446 | 117 ± 107 (15.2) | 1771 ± 385 |
| LS174T (Colorectal-Ca) | 130 ± 14 | 30 ± 3 (5.4) | 160 ± 15 |
| HONE-1 (Nasopharyngeal-Ca) | 219 ± 19 | 71 ± 8 (3.5) | 250 ± 19 |
| DU-145 (Prostate-Ca) | 174 ± 18 | 54 ± 8 (3.1) | 166 ± 12 |
| T98G (Glioblastoma) | 99 ± 9 | 32 ± 4 (3.6) | 115 ± 14 |
| Saos-2 (Osteosarcoma) | 126 ± 22 | 35 ± 6 (3.9) | 138 ± 14 |
| Rat embryo fibroblast | | | |
| CREF (normal rat embryo) | 60 ± 10 | 35 ± 5 (1.7) | 66 ± 7 |
| CREF-ras (transformed) | 147 ± 16 | 25 ± 4 (6.0) | 151 ± 16 |

[a]Logarithmically growing cells were seeded at 1 × 10$^6$ per 100-mm plate and transfected with 10 µg of vector [pREP4 (RSV)] containing no insert, mda-7 (S), or mda-7 (AS). After 24 hr, cells were replated at approximately 2 × 10$^5$ cells per 100-mm plate in medium containing 100 µg/ml of hygromycin. Medium was changed every 3 or 4 days and plates were fixed in formaldehyde and stained with Giemsa at day 14 or 21. Colonies containing 50 or more cells were enumerated. Values shown are the average Hyg$^R$ colonies formed in four to five replicate plates ± S.D.
[b]Values in parentheses indicate fold-decrease in colony formation versus RSV-mda-7 (AS) transfected cells.
[c]MCF-7, T47D, HeLa, LS174T, DU-145 and HONE-1 are human carcinoma (Ca) cell lines isolated from the indicated anatomical site. T98G is a human glioblastoma multiforme cell line. CREF-ras is a Ha-ras (T24) oncogene transformed CREF clone.

In addition to forming fewer colonies, mda-7 (S) colonies are generally smaller in size than corresponding Hyg$^R$ colonies resulting after transfection with the pREP4 vector or mda-7 (AS) constructs (FIG. 1). When transfected into additional human cancer cell lines mda-7 (S) constructs reduce Hyg$^R$ colony formation by 3-to 10-fold (Table 1). These include human breast carcinoma (MCF-7 and T47D), colon carcinoma (LS174T and SW480), nasopharyngeal carcinoma (HONE-1), prostate carcinoma (DU-145), melanoma (H0-1 and C8161), glioblastoma multiforme (GBM-18 and T98G) and osteosarcoma (Saos-2). As observed with HeLa cells, the average sizes of Hyg$^R$ colonies that form after transfection with mda-7 (S) constructs are smaller than those formed following transfection with the empty pREP4 vector or mda-7 (AS) constructs. These results demonstrate that mda-7 is a potent growth suppressing gene when over-expressed in a wide spectrum of histologically distinct human cancers. To determine if mda-7 also inhibits the growth of normal cells and whether this effect is quantitatively similar to that observed with human cancer cells, transient DNA transfection assays were performed with passage 10 to 12 normal human mammary epithelial (HMEC) cells, the normal breast epithelial cell line HBL-100, normal human skin fibroblasts (passage 21) and a cloned normal rat embryo fibroblast cell line (CREF-Trans 6) (7,8). Since HMEC, HBL-100 and normal human skin fibroblasts do not form well-defined colonies at high frequencies, even when using a feeder-layer, the effect on total cell number after transfection with the different RSV constructs and growth for two and three weeks in hygromycin was determined. Using this approach, an approximate 1.1 to 1.6-fold decrease in HMEC, an approximate 1.1 to 1.2-fold decrease in HBL-100 and an approximate 1.3 to 2.1-fold decrease in normal human skin fibroblast cell number was observed (three independent experiments with each cell type) in mda-7 (S) versus mda-7 (AS) or pREP4 vector transfected normal cells, respectively. In contrast, using a similar experimental protocol with T47D human breast carcinoma cells, growth was inhibited following transfection with the mda-7 (S) construct approximately 3.2 to 5.2-fold in comparison with vector-and antisense-transfected cells. In the case of CREF-Trans 6 cells, the difference in $Hyg^R$ colony formation for six independent transfection assays between mda-7 (S) versus mda-7 (AS) and vector transfected cells ranged from 0.5 to 2.8-fold (Table 1). In contrast, transfection of mda-7 (S) constructs into Ha-ras transformed CREF cells reduced colony formation by ~6 to 8-fold (Table 1). These results indicate that mda-7 is quantitatively less effective in reducing growth and colony formation in normal human and normal rodent cells than in human cancer and Ha-ras-transformed rat embryo cells.

Figure 2:
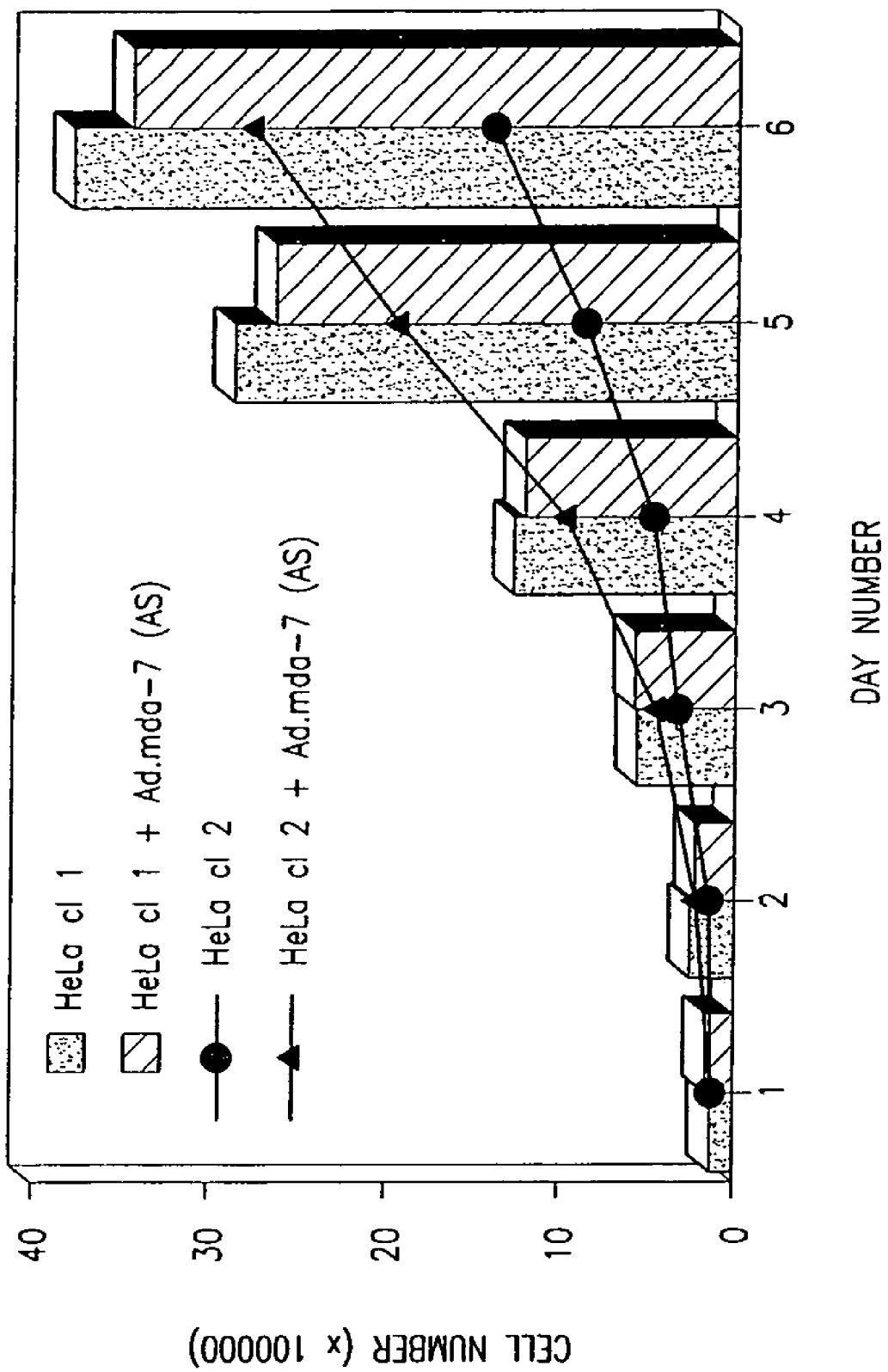
FIG. 2. Effect of antisense mda-7 on monolayer growth of pREP4 vector HeLa cl 1 and mda-7 (S) expressing HeLa cl 2 cells. HeLa cl 1 (pREP4 vector transformed HeLa clone) and HeLa cl 2 (mda-7 expressing HeLa clone) cells were grown in the absence or following infection with 10 plaque forming units/cell with a recombinant type 5 adenovirus (Ads) expressing antisense mda-7 [Ad.mda-7 (AS)]. Results are the average cell number from triplicate samples that varied by ≦10%.

Effect of Stable and Inducible mda-7 Expression and Antisense Inhibition of mda-7 Expression on Cell Growth and the Transformed Phenotype. To determine the reason for low frequency HeLa cell survival after transfection with the mda-7 (S) gene, ten independent $Hyg^R$ colonies were isolated following transfection with the mda-7 (S) construct. of the 10 clones analyzed by Northern blotting for mda-7 expression, 7 clones did not express detectable mda-7 mRNA, 2 clones expressed low levels of mda-7 mRNA and 1 clone (designated HeLa cl 2) displayed high levels of mda-7 mRNA. In contrast, all of the clones displayed comparable levels of $Hyg^R$ and glyceraldehyde 3-phsphate dehydrogenase (GAPDH) gene expression. When compared with parental HeLa cells or an pREP4 vector HeLa clone (designated HeLa cl 1), HeLa cl 2 (mda-7 expressing) cells grew at a reduced rate (FIG. 2). When grown in agar, uncloned HeLa and HeLa cl 1 cells grew with approximately 42% efficiency, whereas HeLa cl 2 (mda-7 expressing) cells grew with approximately 25% efficiency and the average sizes of colonies were smaller than observed with parental HeLa and pREP4 vector HeLa cl 1 cells. These results indicate that HeLa survival after transfection with mda-7 results primarily from the lack of or low levels of mda-7 expression. However, in HeLa cells that stably express elevated mda-7, growth in monolayer culture and anchorage-independence are reduced.

To determine if the reduction in in vitro growth and transformation suppression found in HeLa cl 2 (mda-7 expressing) are a direct consequence of mda-7 expression, an antisense strategy was used to directly inhibit mda-7 expression. A recombinant Ad5 vector containing the mda-7 gene cloned in an antisense orientation [Ad.mda-7 (AS)] was constructed. Infection of HeLa cl 2 (mda-7 expressing), but not HeLa cl 1 (pREP4 vector, non-mda-7 expressing) or parental HeLa, with Ad.mda-7 (AS) increases growth rate and agar cloning efficiency (from approximately 25 to approximately 44%) (FIG. 2). In contrast, the control mutant Ads vector (H5dl434), not containing the mda-7 gene, does not affect monolayer or agar growth of parental HeLa, HeLa cl 1 or HeLa cl 2 cells (data not shown).

Figure 3:
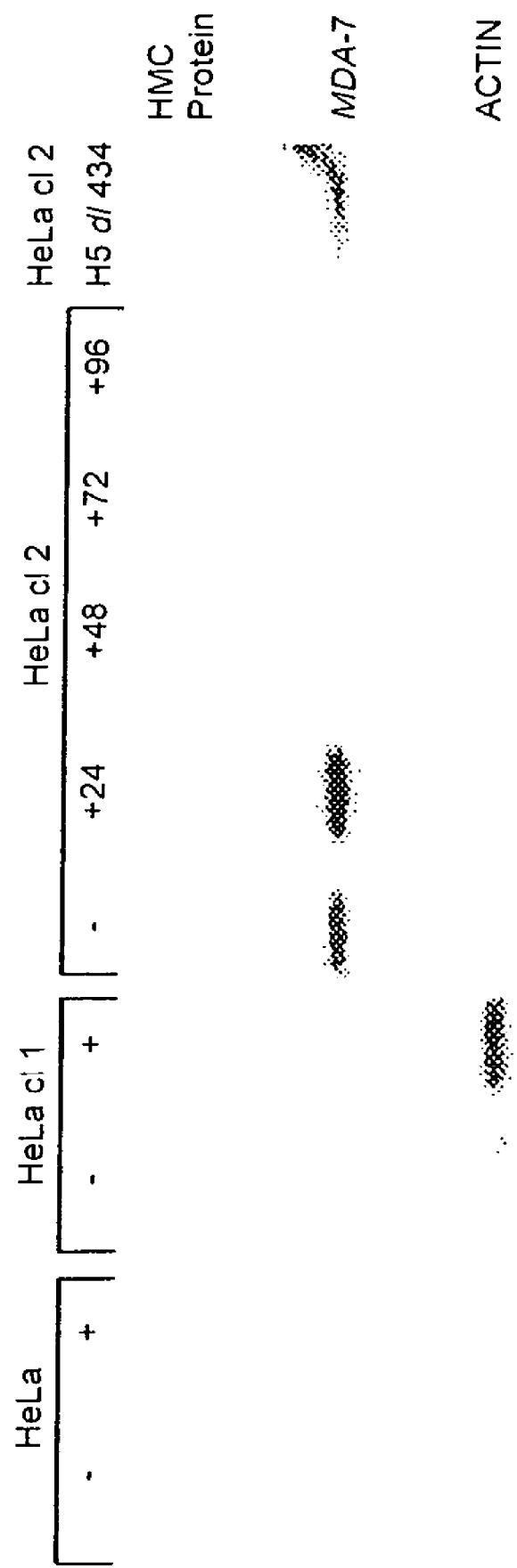
FIG. 3. Effect of antisense mda-7 on the high molecular weight-MDA-7 complexing (HMC) protein, the MDA-7 protein and the actin protein in HeLa, HeLa cl 1, and HeLa cl 2 cells. HeLa and HeLa cl 1 (pREP4 vector transformed HeLa clone) were uninfected (−) or infected (+) with 10 plaque forming units/cell of Ad.mda-7 (AS) for 96 hr labeled with [$^{35}$S] methionine, and the levels of the HMC, MDA-7 and actin proteins were determined by immunoprecipitation analysis. For HeLa cl 2 (mda-7 expressing HeLa clone), the effect of infection with 10 plaque forming units/ml of Ad.mda-7 (AS) on protein levels was determined by immunoprecipitation analysis of [$^{35}$S] methionine labeled cell lysates after +24, +48, +72 and +96 hr. The effect of infection of HeLa cl 2 cells with the control mutant Ad5, H5dl 434, was determined by immunoprecipitation analysis of [$^{35}$S] methionine labeled cell lysates 96 hr after infection with 10 plaque forming units/cell.

Using mda-7-specific peptide antibodies produced in rabbits and immunoprecipitation analyses, the HeLa cl 2 (mda-7 expressing) cells contain elevated levels of the MDA-7 approximately 24 kDa protein and a high molecular weight complexing (HMC) protein of approximately 90 to 110 kDa (FIG. 3). Infection with Ad.mda-7 (AS), but not the H5dl434 control non-mda-7 expressing virus, results in a temporal decrease in both the ~24 kDa MDA-7 protein and the HMC protein (21) (FIG. 3). Reduced levels of both proteins are seen by 48 hr and remain suppressed over a 96 hr period after infection with Ad.mda-7 (AS). In contrast, actin levels remain unaltered following viral infection. These findings indicate that antisense inhibition of MDA-7 protein expression in HeLa cl 2 (mda-7 expressing) can directly extinguish mda-7 induced growth suppression and inhibition in anchorage-independent growth.

Figure 4A:
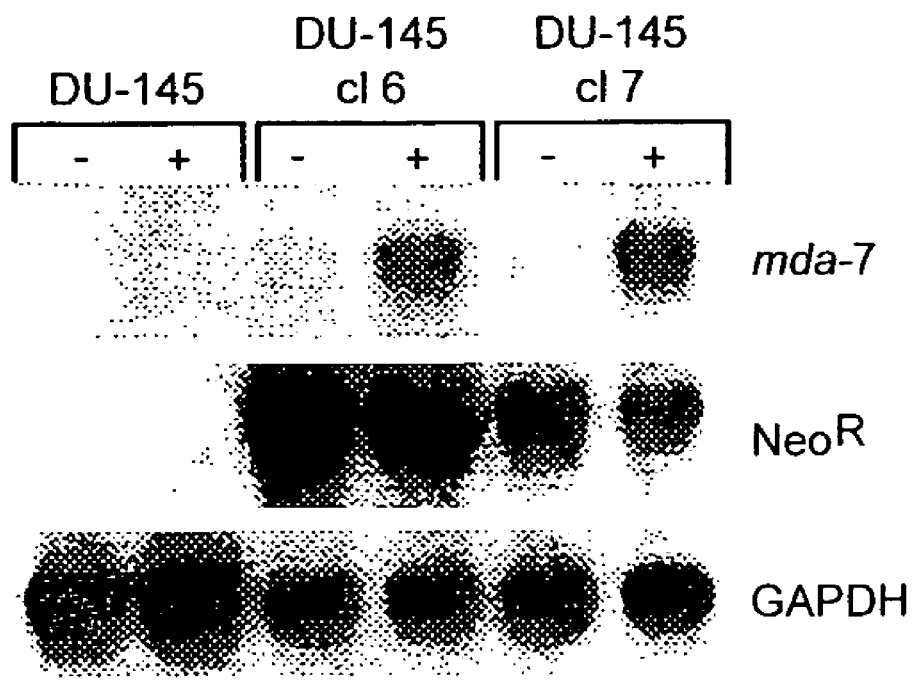
FIGS. 4A & 4B Synthesis of mda-7 RNA and protein in DU-145 clones containing a DEX-inducible mda-7 gene.
Figure 4B:
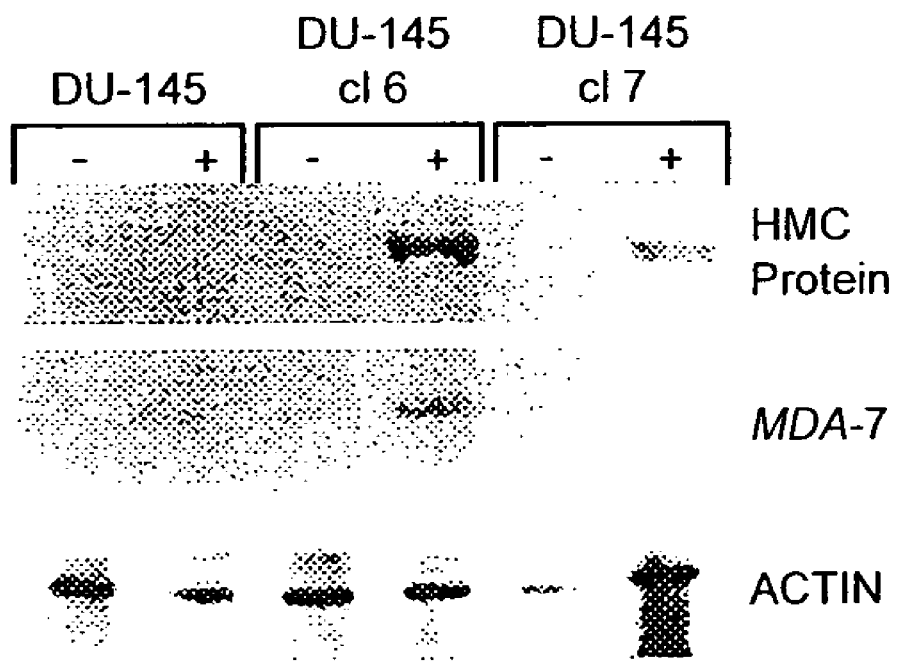

To confirm the suppressive effect of mda-7 on cell growth, DU-145 human prostate cancer cells were engineered to express a DEX-inducible mda-7 gene. When DU-145 cl 6 or cl 7 cells [containing a DEX-inducible mda-7 (S) gene], but not parental DU-145 cells, are grown for 24 to 96 hr in the presence of $10^{-6}$ M DEX, mda-7 mRNA and protein (including the HMC protein) are induced (FIG. 4). In contrast, DEX does not alter neomycin resistance ($Neo^R$)gene expression in DU-145 cl 6 and cl 7 cells or GAPDH expression in any of the cells tested (FIG. 4). Induction of mda-7 expression in DU-145 cl 6 and cl 7 cells by growth in $10^{-6}$ M DEX results in approximately 50% reduction in cell number after 96 hr versus growth in the absence of DEX. In contrast, no significant growth inhibition occurs when parental DU-145 or pMAMneo vector transformed DU-145 cells are grown for 96 hr in medium containing $10^{-6}$ M DEX (data not shown). These data indicate that ectopic expression of mda-7 can directly alter cell growth in prostate cancer cells.

Experimental Discussion

Subtraction hybridization identified mda genes with elevated expression in growth arrested and terminally differentiated human melanoma cells (13,14,21). Determining the function of these mda genes will be paramount in defining the molecular basis of growth control and terminal differentiation in human melanoma and other cell types. The mda-7 gene (14,21) is now shown to be a ubiquitous growth suppressing gene when transiently or stably expressed in a wide array of human cancer cell lines. This finding extends previous observations indicating growth inhibitory properties of the MDA-7 protein in human melanoma cells (21). In contrast to its effects on cancer cells, transfection of mda-7 into normal human mammary epithelial, normal human skin fibroblast and normal rat embryo fibroblast cells results in quantitatively less growth suppression. Like another mda gene, mda-6 (p21), mda-7 expression is also inversely correlated with melanoma progression, with elevated levels of both mda-6 (p21) and mda-7 present in normal human melanocytes relative to metastatic human melanoma cells (14-16,21). Since normal melanocytes still retain proliferative capacity, although at a reduced rate relative to melanoma cells, it is possible that both mda-6 (p21) and mda-7 function as negative regulators of the progression phenotype in melanocyte/melanoma lineage cells (14-16,21). Moreover, the elevated expression of both mda-6 (p21) and mda-7 in terminally differentiated and irreversibly growth arrested human melanoma cells, suggests that these genes may also be important regulators of the terminal differentiation phenotype (13-16,21).

The mechanism by which mda-7 elicits its growth suppressive effects on human cancer cells is not presently known. The structure of mda-7 does not provide insight into potential function, since no sequence motifs are present that would suggest a potential mode of action. The effect of mda-7 on cell growth can be distinguished from the extensively studied tumor suppressor gene p53 (33,34). Transient expression of p53 in the mutant p53 containing T47D human breast carcinoma cell line results in growth suppression, whereas transfection of a wild-type p53 gene into the wild-type p53 containing MCF-7 human breast carcinoma cell line does not induce growth inhibition (34). In contrast, mda-7 induces similar growth suppression in both T47D and MCF-7 cells (Table 1). Growth inhibition by mda-7 can also be disassociated from that observed with the retinoblastoma gene (pRB), the pRb-associated p107 gene and the putative tumor suppressor gene p16$^{ink4}$ (25,35). Overexpression of pRb and p107 inhibit cellular proliferation in specific cell types and in a cell cycle-dependent manner (35-37). Transfection of pRb or p107 into the human glioblastoma cell line T98G that contains an apparently normal RB gene (25) does not induce growth suppression (35,37), whereas transient mda-7 (S) expression reduces T98G colony formation (Table 1). At the present time, the growth inhibitory effect of mda-7 cannot be distinguished from growth suppression induced by the RB family member p130/pRb2, which also inhibits proliferation in T98G cells (25). The p16$^{ink4}$ gene induces growth arrest in cells containing a functional RB gene (35,37), whereas mda-7 growth suppression occurs in cells containing normal, abnormal or non-functional RB genes. Transfection of mda-7 into the DU-145 human prostate carcinoma cell line that contains a mutated RB gene (38) and Saos-2 human osteosarcoma cells that do not express RB (or wild-type p53) results in an inhibition in colony formation (Table 1). Similarly, induction of mda-7 expression in stable DEX-inducible mda-7 transformed DU-145 clones results in growth suppression. These findings indicate a lack of dependence on a functional RB gene for growth inhibition by mda-7. Taken together these studies demonstrate that the inhibitory effect of mda-7 occurs by a mechanism that is distinct from the mode of action of the two most extensively studied tumor suppressor genes, p53 and pRb, and the putative tumor suppressor gene p16$^{ink4}$.

Several genes have been identified that display elevated expression as a function of growth arrest or DNA damage in mammalian cells (39,40). Three growth arrest and DNA damage inducible (gadd) genes, gadd45, gadd153 and gadd34, the closely related myeloid differentiation primary response (MyD118) gene (41) and the wild-type p53 inhibiting gene mdm-2 (42) are upregulated in cells by treatment with the DNA damaging agent methyl methanesulfonate (MMS) (40). The gadd45 and growth arrest-specific gene (gas1) (43,44) are induced by maintaining cells at confluence, serum-starving cells or growing cells in low serum (40,43,44). In contrast, mda-7 mRNA expression is not induced in human melanoma cells following treatment with methyl methane sulfonate (MMS) or after maintaining cells at confluence (21). Moreover, only a small increase in mda-7 mRNA expression occurs in H0-1 human melanoma cells following growth in serum-free medium for 96 hr (21). The difference in regulation of mda-7 versus the gadd, MyD118 and gas-1 genes indicates that mda-7 may represent a new class of growth arresting genes.

In summary, a negative growth regulator, mda-7, is described that induces growth suppression in human cancer cells containing both normal and mutated p53 and RB genes. Characterization of the genomic structure of mda-7 will be important in determining if this gene normally functions as a tumor suppressor gene and whether alterations are present in this gene in tumor versus normal cells. Identification of the promoter region of mda-7 will also permit an analysis of the mechanism by which this gene is differentially expressed and inducible by IFN-β plus MEZ in specific cell types. of potential importance and warranting expanded studies, is the finding that mda-7 is more growth inhibitory toward cancer and transformed cells than normal cells. In this context, mda-7 could prove useful as part of a gene-based interventional strategy for cancer therapy, in an analogous manner as the wild-type p53 gene is currently being tested for efficacy in the therapy of specific human malignancies.

REFERENCES

1. Fisher, P. B. (1984) in *Tumor Promotion and Cocarcinogenesis in Vitro: Mechanisms of Tumor Promotion*, ed. Slaga, T. J., (CRC, Boca Raton, Fla.), vol. 3, pp. 57-123.
2. Bishop, J. M. (1991). *Cell* 64, 235-248.
3. Knudson, A. G. (1991). *Proc. Natl. Acad. Sci. USA* 90, 10914-10921.
4. MacLachlan, T. K., Sang, N. & Giordano, A. (1995). *Crit. Rev. Eukaryotic Gene Express.* 5, 127-156.
5. Sang, N., Baldi, A. & Giordano, A. (1995). *Mol. Cell. Differ.* 3, 1-29.
6. Barbacid, M. (1987). *Annu. Rev. Biochem.* 56, 779-827.
7. Bos, J. (1989). *Cancer Res.* 49, 4682-4689.
8. Su, Z.-z., Olsson, C. A., Zimmer, S. G. & Fisher, P. B. (1992). *Anticancer Res.* 12, 297-304.
9. Shen, R., Su, Z.-z., Olsson, C. A. & Fisher, P. B. (1995). *Proc. Natl. Acad. Sci. USA* 92, 6778-6782.
10. Noda, M., Kitayama, H., Matsuzaki, T., Sugimoto, Y., Okayama, H., Bassin, R. H. & Ikawa, Y. (1988) *Proc. Natl. Acad. Sci. USA* 86, 162-166.
11. Kitayama, H., Sugimoto, Y., Masuzaki, T., Ikawa, Y. & Noda, M. (1989). *Cell* 56, 77-84.
12. Lin, J., Su, Z.-z., Grunberger, D., Zimmer, S. G. & Fisher, P. B. (1994). *Int. J. Oncol.* 5, 5-15.
13. Jiang, H. & Fisher, P. B. (1993). *Mol. Cell. Differ.* 1, 285-299.
14. Jiang, H., Lin, J. & Fisher, P. B. (1994). *Mol. Cell. Differ.* 2, 221-239.
15. Jiang, H., Lin, J., Su, Z.-z., Herlyn, M., Kerbel, R. S., Weissman, B. E., Welch, D. R., & Fisher, P. B. (1995) *Oncogene* 10, 1855-1864.
16. Jiang, H., Lin, J., Su, Z.-z. & Fisher, P. B. (1996). *Mol. Cell. Differ.* 4, 67-89.
17. Xiong, Y., Hannon, G. J., Zhang, H., Casso, D., Kobayashi, R. & Beach, D. (1993). *Nature* (London) 366, 701-704.
18. El-Deiry, W. S., Tokino, T., Velculescu, V. E., Levy, D. B., Parsons, R., Trent, J. M., Lin, D., Mercer, W. E., Kinzler, K. W. & Vogelstein, B. (1993). *Cell* 75, 817-825.
19. Harper, J. W., Adami, G. R., Wei, N., Keyomarsi, K. & Elledge, S. J. (1993). *Cell* 75, 805-816.
20. Noda, A., Ning, Y., Venable, S. F., Pereira-Smith, O. M. & Smith, J. R. (1994). *Exp. Cell Res.* 211, 90-98.
21. Jiang, H., Lin, J. J., Su, Z.-z., Goldstein, N. I. & Fisher, P. B. (1995). *Oncogene* 11, 2477-2486.
22. Leon, J. A., Mesa-Tejada, R., Gutierrez, M. C., Estabrook, A., Greiner, J. W., Schlom, J. & Fisher, P. B. (1989). *Anticancer Res.* 9, 1639-1648.
23. Kantor, J., Tran, R., Greiner, G., Pestka, S., Fisher, P. B., Shively, J. E. & Schlom, J. (1989). *Cancer Res.* 49, 2651-2655.
24. Leon, J. A., Guttierez, M. C., Jiang, H., Estabrook, A., Waxman, S. & Fisher, P. B. (1992). *Cancer Immunol. Immunother.* 35, 315-324.
25. Claudio, P. P., Howard, C. M., Baldi, A., De Luca, A., Fu, Y., Condorelli, G., Sun, Y., Colburn, N., Calabretta, B. & Giordano, A. (1994). *Cancer Res.* 54, 5556-5560.
26. Fisher, P. B., Babiss, L. E., Weinstein, I. B. & Ginsberg, H. S. (1982). *Proc. Natl. Acad. Sci. U.S.A.* 79, 3527-3531.

27. Boylon, J., Shih, T., Fisher, P. B. & Zimmer, S. G. (1992). *Mol. Carcinog.* 5, 118-128.
28. Falck-Pedersen, E., Heinflink, M., Alvira, M., Nussenzweig, D. R. & Gershengorn, M. C. (1994). *Mol. Pharmacol.* 45, 684-689.
29. Graham, F. L., Smiley, J., Russell, W. C. & Nairn, R. (1977). *J. Gen. Virol.* 36, 59-72.
30. McGrory, W. J., Bautista, D. S. & Graham, F. L. (1988). *Virology* 163, 614-617.
31. Volkert, F. C. & Young, C. S. H. (1983). *Virology* 125, 175-193.
32. Grodzicker, T. & Klessig, D. (1980). *Cell* 21, 453-463.
33. Baker, S. J., Markowitz, S., Fearon, E. R., Wilson, J. K. V. & Vogelstein, B. (1990). *Science* 249, 912-915.
34. Mercer, W. E. (1992). *Crit. Rev. Eukaryotic Gene Expression* 2, 251-263.
35. Medema R. H., Herrera, R. E., Lam F. & Weinberg, R. A. (1995). *Proc. Natl. Acad. Sci. USA* 92, 6289-6293.
36. Grana, X. & Reddy, E. P. (1995). *Oncogene* 11, 211-220.
37. Zhu, L., van den Heuvel, S., Helin, K., Fattaey, A., Ewen, M., Livingston, D., Dyson, N. & Harlow, E. (1993). *Genes & Dev.* 7, 1111-1125.
38. Bookstein, R., Shew, J. Y., Chen, P. L., Scully, P. & Lee, W. H. (1990). *Science* 247, 712-715.
39. Fornace, A. J., Jr., Alamo, I. J., Jr. & Hollander, M. C. (1988). *Proc. Natl. Acad. Sci. USA* 85, 8800-8804.
40. Zhan, Q., Lord, K.A., Alamo, I., Jr., Hollander, M. C., Carrier, F., Ron, D., Kohn, K. W., Hoffman, B., Liebermann, D. A. & Fornace, A. J., Jr. (1994). *Mol. Cell. Biol.* 14, 2361-2371.
41. Abdollahi, A., Lord, A., Hoffman-Liebermann, B. & Liebermann, D. (1991). *Oncogene* 6, 165-167.
42. Momand, J., Zambetti, G. P., Olson, D. C., George, D. & Levine, A. J. (1992). *Cell* 69, 1237-1245.
43. Schneider, C., King, R. M. & Philipson, L. (1988). *Cell* 54, 787-793.
44. Del Sal, G., Ruaro, M. E., Philipson, L. & Schneider, C. (1992). *Cell* 70, 595-607.
45. Sambrook, J., et al.(1989) *Molecular Cloning: a laboratory manual. Second Edition*. Cold Spring Harbor Laboratory Press (1989).

Second Series of Experiments

Melanoma Differentiation Associated Gene-7 (mda-7) in a Recombinant Adenovirus Inhibits the Growth of Established Human Tumors in Nude Mice Previous studies document that ectopic expression of mda-7 in human tumor cells of diverse origins inhibits growth, as documented by a decrease in colony formation in monolayer culture (Jiang et al., PNAS, 93: 9160-9165, 1996). In contrast, mda-7 does not significantly alter the growth of normal human epithelial or fibroblast cells. These observations support the hypothesis that mda-7 is a ubiquitous cancer growth suppressor gene.

The ability of mda-7 to selectively inhibit cancer cell growth suggests that this gene might provide therapeutic benefits in the treatment of human cancers. To explore this possibility a replication-defective adenovirus expressing mda-7 has been generated. The protocols were similar to those used to construct an adenovirus expressing antisense mda-7, Ad.mda-7 AS (Jiang et al., PNAS, 93: 9160-9165, 1996). The recombinant replication-defective Ad.mda-7 S was produced in two steps. First, the mda-7 gene was cloned in a sense orientation into a modified Ad expression vector pAd.CMV. This virus contains, in order, the first 355 bp from the left end of the Ad genome, the cytomegalovirus (CMV) immediate early promoter, DNA encoding a poly A signal sequence from the beta globin gene, and approximately 3 kbp of adenovirus sequence extending from within the E1B coding region. This arrangement allows high level expression of the cloned sequence by the CMV immediate early gene promoter, and appropriate RNA processing. The recombinant virus was created in vivo in 293 cells by homologous recombination between mda-7 containing vector and JM17, which contains the whole of the Ad genome cloned into a modified version of pBR322. JM17 gives rise to Ad genomes in vivo but they are too large to package. This constraint is relieved by recombination with the vector to create a packageable genome, containing the gene of choice. The recombinant virus is replication defective in human cells except 293, which express adenovirus E1A and E1B. Following transfection of the two plasmids, infectious virus was recovered, the genomes were analyzed to confirm the recombinant structure, and then virus was plaque purified, all by standard procedures.

As observed with transfection with mda-7, infection of diverse human cancer cell lines, but not normal cell lines, with Ad.mda-7 S inhibited growth. These results demonstrate that this virus retains properties observed with the mda-7 plasmid construct. In many cancer cells, including breast carcinoma (MCF-7 and T47D), glioblastoma (GBM-18 and T98G) and melanoma (H0-1 and C8161), infection with Ad.mda-7 S resulted in the induction of programmed cell death (apoptosis). This effect was not elicited in normal cells even after infection with high multiplicities of infection (100 pfu/cell) with Ad.mda-7 S. In other cancer cell types, growth suppression (as indicated by a suppression in colony formation in monolayer culture) was apparent without signs of apoptosis, as indicated by nuclear morphology changes, formation of nucleosomal ladders or a positive TUNEL reaction. These results indicate that the Ad.mda-7 S virus can selectively inhibit the growth of human cancer cells in vitro. Moreover, in specific cancer cell types growth suppression correlates with induction of apoptosis. These observations suggest that inhibition in cancer growth induced by mda-7 can occur by multiple pathways.

Nude mouse human tumor xenograft models were used to determine if Ad.mda-7 S can inhibit the growth of human cancer cells in vivo. Athymic nude mice, obtained from Taconic Labs, were injected subcutaneously with one million human cervical carcinoma (HeLa) cells in PBS mixed with matrigel (final volume 0.4 ml; ratio of matrigel to PBS 1:1). Tumors were allowed to grow until they reached an average volume of 100 to 200 mm$^3$ (10 to 21 days post inoculation). Mice were then randomized and divided into two groups: Group 1: replication-defective Ad lacking the mda-7 gene; null virus (null); and Group 2: Ad.mda-7 S. Treatment consisted of intratumoral injections of the null or Ad.mda-7 S (100 µl at 4 sites/injection) three times a week for 4 weeks. Tumors were measured twice to three times weekly with a caliper. Tumor volumes were calculated using the formula: pi/6×larger diameter×(smaller diameter)$^2$. After 4 weeks of therapy, animals were followed for an additional week and sacrificed. Final tumor volume divided by initial tumor volume equals tumor volume ratio which is defined as a measure of cancer progression.

Figure 5:
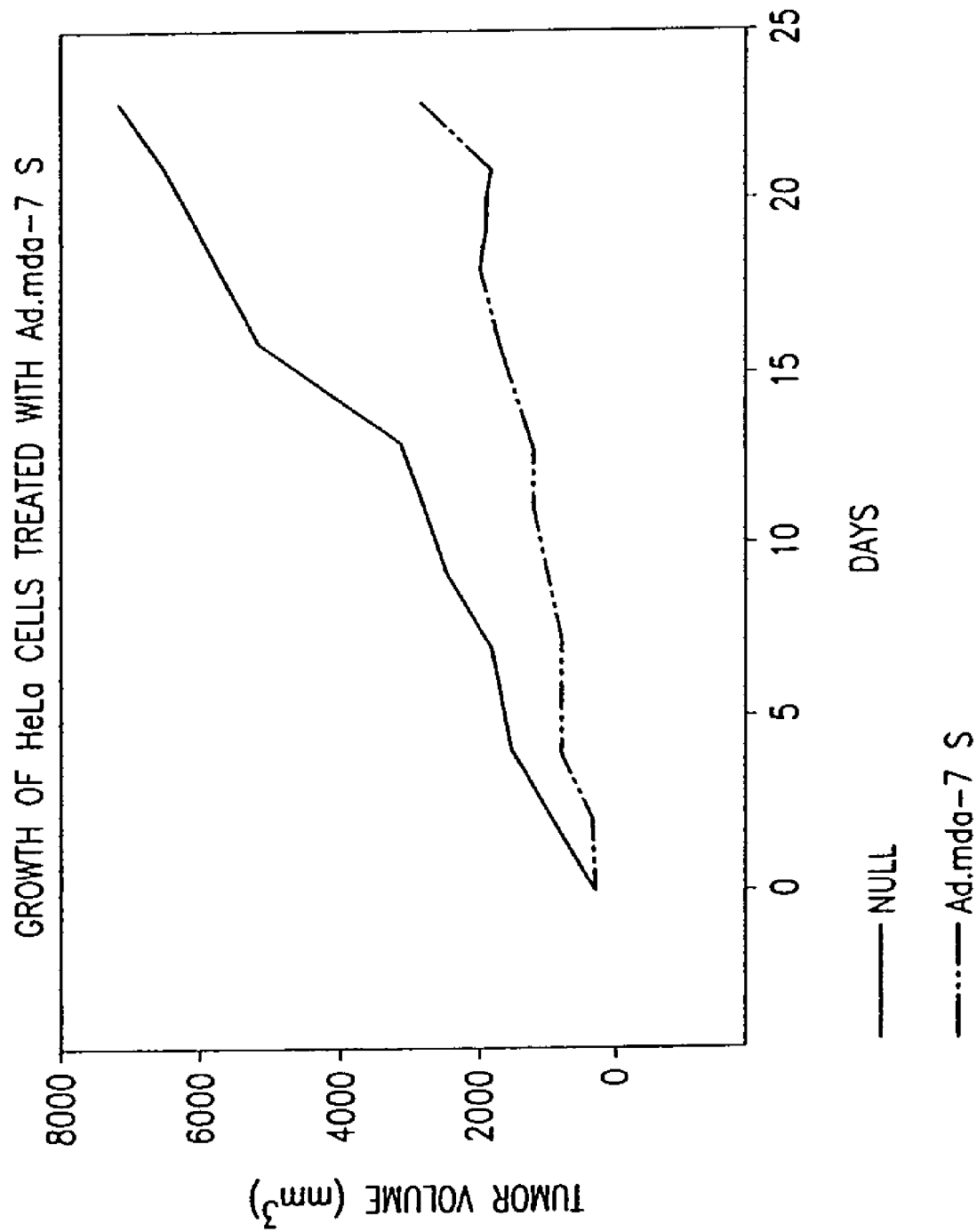
FIG. 5 Inhibition of growth of established human cervical cancer (HeLa) exenografts in athymic nude mice.
Figure 6:
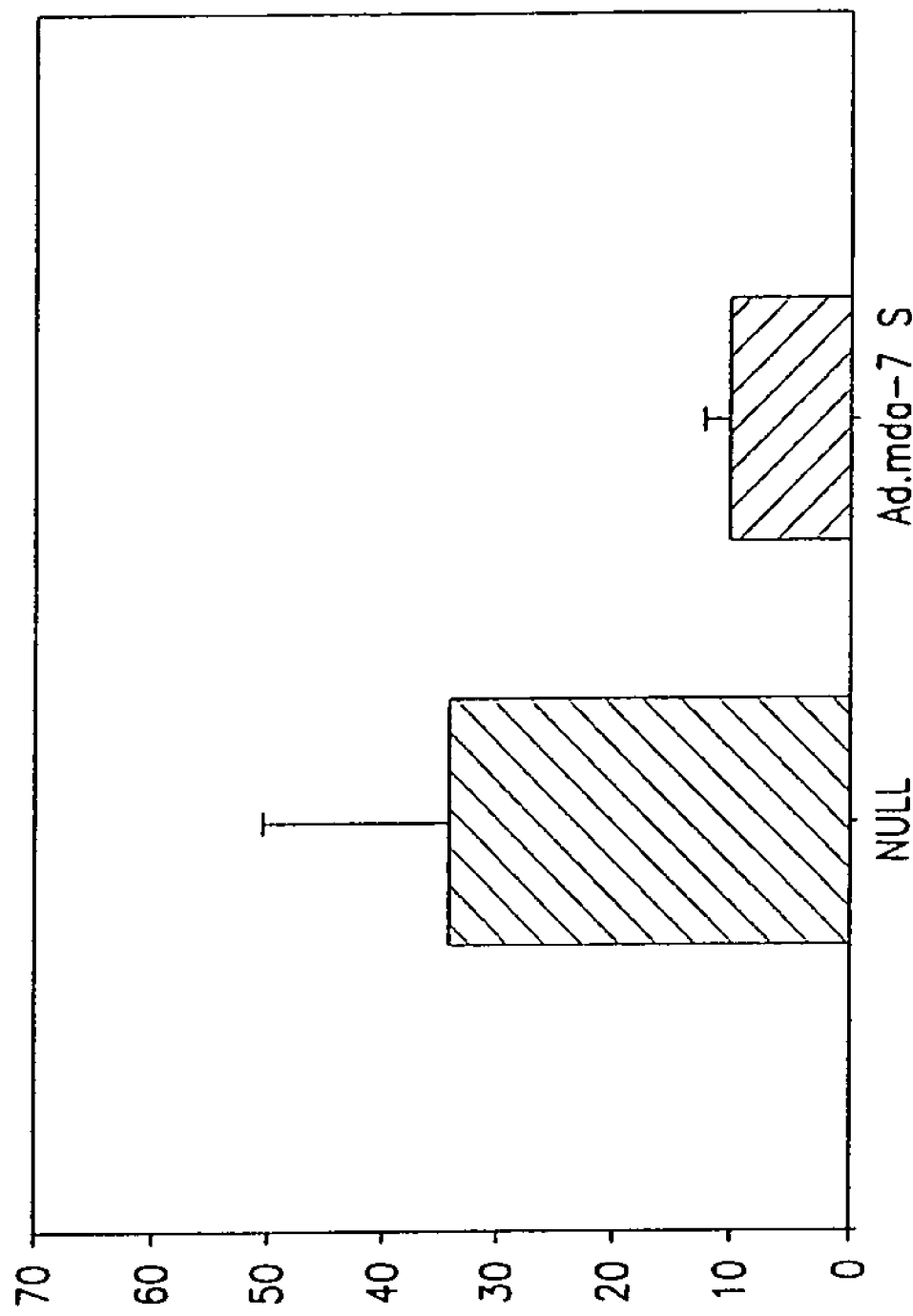
FIG. 6 Effect of Ad.mda-7 S on HeLa tumor volume ratios. The result indicates that Ad.mda-7 S can inhibit tumor progression in vivo in nude mice.

Well-established HeLa xenografts, treated with Ad.mda-7 S, were growth inhibited over the course of the study, whereas tumors treated with the null virus continued to grow progressively (FIGS. 5 and 6). The mda-7 inhibitory effect was significant with a p value <0.05. This study was repeated and similar results were obtained. This data suggest that ectopic expression of mda-7 may provide therapeutic benefit for the treatment of human cancer. Experiments are now in progress using established human breast cancer tumors, MCF-7 and T47D, in nude mice.

What is claimed is:

1. A method for inhibiting an increase in the volume of a tumor in a subject, comprising administering, to the subject, by intratumoral injection, a nucleic acid comprising a human melanoma differentiation associated-7 gene operably linked to a promoter element, in an amount effective to inhibit an increase in tumor volume in the subject, wherein the tumor is a cancer type selected from the group consisting of a breast cancer, a cervical cancer, a prostate cancer, a nasopharyngeal cancer, and a lung cancer.

* * * * *